(12) United States Patent
Steinberg et al.

(10) Patent No.: US 11,419,483 B2
(45) Date of Patent: Aug. 23, 2022

(54) STEERABLE ULTRASOUND ATTACHMENT FOR ENDOSCOPE

(71) Applicant: ENDOSOUND, LLC, Boca Raton, FL (US)

(72) Inventors: Stephen E. Steinberg, Boca Raton, FL (US); Scott Sutherland Corbett, III, Portland, OR (US)

(73) Assignee: EndoSound, Inc., Boca Raton, FL (US)

( * ) Notice: Subject to any disclaimer, the term of this patent is extended or adjusted under 35 U.S.C. 154(b) by 0 days.

(21) Appl. No.: 17/193,553

(22) Filed: Mar. 5, 2021

(65) Prior Publication Data
US 2021/0212662 A1    Jul. 15, 2021

Related U.S. Application Data

(63) Continuation of application No. 16/523,971, filed on Jul. 26, 2019, which is a continuation-in-part of (Continued)

(51) Int. Cl.
*A61B 1/00* (2006.01)
*A61B 8/00* (2006.01)
(Continued)

(52) U.S. Cl.
CPC ........ *A61B 1/00101* (2013.01); *A61B 1/0051* (2013.01); *A61B 1/00098* (2013.01);
(Continued)

(58) Field of Classification Search
CPC ............ A61B 1/00089; A61B 1/00098; A61B 1/0008; A61B 1/00135; A61B 1/0014;
(Continued)

(56) References Cited

U.S. PATENT DOCUMENTS 4,802,487 A    2/1989   Martin et al.
5,257,628 A  * 11/1993  Ishiguro ................. A61B 8/445
                                              600/463
(Continued)

FOREIGN PATENT DOCUMENTS

JP    WO2018016487 A1    1/2018

OTHER PUBLICATIONS

Manta, Rafaele et al., Clinical Clip: EUS Fine Needle Aspiration Procedure, Endoscopy Unit Nuovo Ospedale Civile Sant'Agostino Estense, Baggiovara, Modena, Italy, Cook Endoscopy 2009.
(Continued)

*Primary Examiner* — Ryan N Henderson
(74) *Attorney, Agent, or Firm* — K&L Gates LLP

(57) ABSTRACT

An endoscope add-on assembly adapted to be attached to a target endoscope. The assembly includes an ultrasound imaging sub-assembly, including a communications cable connected to an ultrasound imaging head and an imaging head movement sub-assembly, including a conduit, holding a tension member that is attached to the ultrasound imaging head. Further included are connective elements, adapted to permit the endoscope add-on assembly to be attached to the target endoscope. Finally, the imaging head movement sub-assembly is detachable from the ultrasound imaging sub-assembly, thereby permitting the imaging head movement subassembly to be processed separately from the ultrasound imaging sub-assembly, after use.

12 Claims, 13 Drawing Sheets

Related U.S. Application Data application No. PCT/US2019/027331, filed on Apr. 12, 2019, which is a continuation of application No. 15/951,347, filed on Apr. 12, 2018, now Pat. No. 10,363,014.

(51) Int. Cl.
| | |
|---|---|
| *A61B 1/005* | (2006.01) |
| *A61B 10/04* | (2006.01) |
| *A61B 17/00* | (2006.01) |
| *A61B 8/12* | (2006.01) |
| *A61B 1/05* | (2006.01) |
| *A61B 1/018* | (2006.01) |
| *A61B 1/273* | (2006.01) |

(52) U.S. Cl.
CPC .......... *A61B 8/4422* (2013.01); *A61B 8/4466* (2013.01); *A61B 10/04* (2013.01); *A61B 1/00103* (2013.01); *A61B 1/00133* (2013.01); *A61B 1/00135* (2013.01); *A61B 1/018* (2013.01); *A61B 1/053* (2013.01); *A61B 1/273* (2013.01); *A61B 8/12* (2013.01); *A61B 8/445* (2013.01); *A61B 8/4411* (2013.01); *A61B 2010/045* (2013.01); *A61B 2017/0034* (2013.01)

(58) Field of Classification Search
CPC ..... A61B 1/00174; A61B 8/12; A61B 8/4444; A61B 8/4461; A61B 10/04; A61B 2017/00296
See application file for complete search history.

(56) References Cited

U.S. PATENT DOCUMENTS

| | | | |
|---|---|---|---|
| 5,499,630 A | | 3/1996 | Susumu |
| 5,569,157 A | * | 10/1996 | Nakazawa ............ A61B 1/018 600/106 |
| 5,596,991 A | * | 1/1997 | Tanaka ................. A61B 8/4461 600/459 |
| 5,873,828 A | * | 2/1999 | Fujio .................... A61B 1/0051 600/459 |
| 6,099,464 A | | 8/2000 | Shimizu et al. |
| 6,171,249 B1 | * | 1/2001 | Chin .................. A61B 17/3403 600/143 |
| 6,224,555 B1 | * | 5/2001 | Ouchi .................. A61B 8/0841 600/439 |
| 6,409,666 B1 | | 6/2002 | Ito |
| 6,461,304 B1 | * | 10/2002 | Tanaka ..................... A61B 8/12 600/462 |
| 6,485,425 B2 | * | 11/2002 | Seward ................. A61B 5/6826 600/459 |
| 7,455,641 B2 | * | 11/2008 | Yamada ........... A61B 17/22012 601/2 |
| 7,771,349 B2 | | 8/2010 | Kohno |
| 8,303,508 B2 | | 11/2012 | Wakabayashi et al. |
| 8,657,749 B2 | | 2/2014 | Sato |
| 8,708,931 B2 | | 4/2014 | Takeuchi et al. |
| 8,827,922 B2 | | 9/2014 | Aoki et al. |
| 8,852,112 B2 | * | 10/2014 | Bielewicz ................ A61B 8/12 600/463 |
| 8,864,675 B2 | * | 10/2014 | Dietz .................. A61B 8/4461 600/463 |
| 8,870,778 B2 | | 10/2014 | Tsutaki et al. |
| 8,900,152 B2 | | 12/2014 | Ogawa et al. |
| 9,332,961 B2 | * | 5/2016 | Ogawa ..................... A61B 8/12 |
| 9,993,138 B2 | * | 6/2018 | Hashiguchi .............. A61B 1/04 |
| D822,827 S | | 7/2018 | Hosogoe |
| D822,828 S | | 7/2018 | Hosogoe |
| D822,829 S | | 7/2018 | Hosogoe |
| 10,045,758 B2 | * | 8/2018 | Marmor ................ A61B 8/4254 |
| 10,070,880 B2 | * | 9/2018 | Bagwell ................. A61B 17/29 |
| 10,363,014 B1 | * | 7/2019 | Steinberg ................. A61B 8/12 |
| 2001/0031923 A1 | * | 10/2001 | Seward ................ G10K 11/004 600/459 |
| 2005/0027310 A1 | * | 2/2005 | Yamada ................. A61B 1/042 606/171 |
| 2007/0299437 A1 | * | 12/2007 | Podmore ............ A61B 1/00087 606/41 |
| 2009/0093725 A1 | | 4/2009 | Sato |
| 2009/0292199 A1 | * | 11/2009 | Bielewicz .............. A61B 8/445 600/459 |
| 2010/0280316 A1 | * | 11/2010 | Dietz .................. A61B 17/3478 600/101 |
| 2011/0166455 A1 | * | 7/2011 | Cully .................... A61B 8/4245 600/463 |
| 2012/0226165 A1 | * | 9/2012 | Ogawa .................. A61B 8/445 600/462 |
| 2013/0102841 A1 | * | 4/2013 | Milsom .............. A61B 17/0401 600/37 |
| 2013/0137990 A1 | * | 5/2013 | Tsuruta .............. A61B 1/00087 600/466 |
| 2013/0225995 A1 | * | 8/2013 | Hashiguchi ............ A61B 1/307 600/459 |
| 2014/0114195 A1 | | 4/2014 | Inui et al. |
| 2014/0296848 A1 | * | 10/2014 | Chang ................ A61B 1/00101 606/41 |
| 2014/0309683 A1 | * | 10/2014 | Bagwell ................. A61B 17/29 606/207 |
| 2015/0025315 A1 | * | 1/2015 | Nishina .............. A61B 10/0275 600/104 |
| 2015/0087994 A1 | | 3/2015 | Matsuno et al. |
| 2016/0206180 A1 | | 7/2016 | Hosogoe |
| 2016/0262722 A1 | * | 9/2016 | Marmor ................ A61B 8/4254 |
| 2016/0309993 A1 | | 10/2016 | Hosogoe |
| 2017/0112361 A1 | * | 4/2017 | Surti .................. A61B 1/00101 |
| 2017/0164815 A1 | * | 6/2017 | Smith .................... A61B 1/273 |
| 2017/0290566 A1 | | 10/2017 | Hosogoe |
| 2017/0340308 A1 | * | 11/2017 | Cermak .................... A61B 8/12 |
| 2018/0168541 A1 | * | 6/2018 | Kitahara ............ A61B 1/00096 |
| 2019/0059702 A1 | | 2/2019 | Hosogoe |
| 2019/0117045 A1 | | 4/2019 | Hosogoe |
| 2019/0133558 A1 | * | 5/2019 | Morimoto ........... A61B 8/4466 |
| 2019/0223696 A1 | | 7/2019 | Hosogoe |
| 2019/0223698 A1 | | 7/2019 | Hosogoe |
| 2019/0231173 A1 | | 8/2019 | Hosogoe |
| 2019/0239726 A1 | * | 8/2019 | Hiraoka ............. A61B 1/00098 |
| 2019/0357883 A1 | * | 11/2019 | Steinberg ............ A61B 8/4466 |
| 2021/0059507 A1 | * | 3/2021 | Yamaya ................ A61B 1/018 |
| 2021/0068628 A1 | * | 3/2021 | Yamaya ................ A61B 1/0052 |
| 2021/0212662 A1 | * | 7/2021 | Steinberg ............. A61B 8/4422 |

OTHER PUBLICATIONS

International Search Report and Written Opinion of PCT application PCT/US2019/027331 issued by the European patent office.
Results of the Partial International Search for PCT/US2019/027331 issued by the European Patent Office.
Korc, Paul et al., ERCP Tissue Sampling, www.giejournal.org, vol. 84, No. 4 : 2016 Gastrointestinal Endoscopy; Accepted Apr. 27, 2016.

* cited by examiner

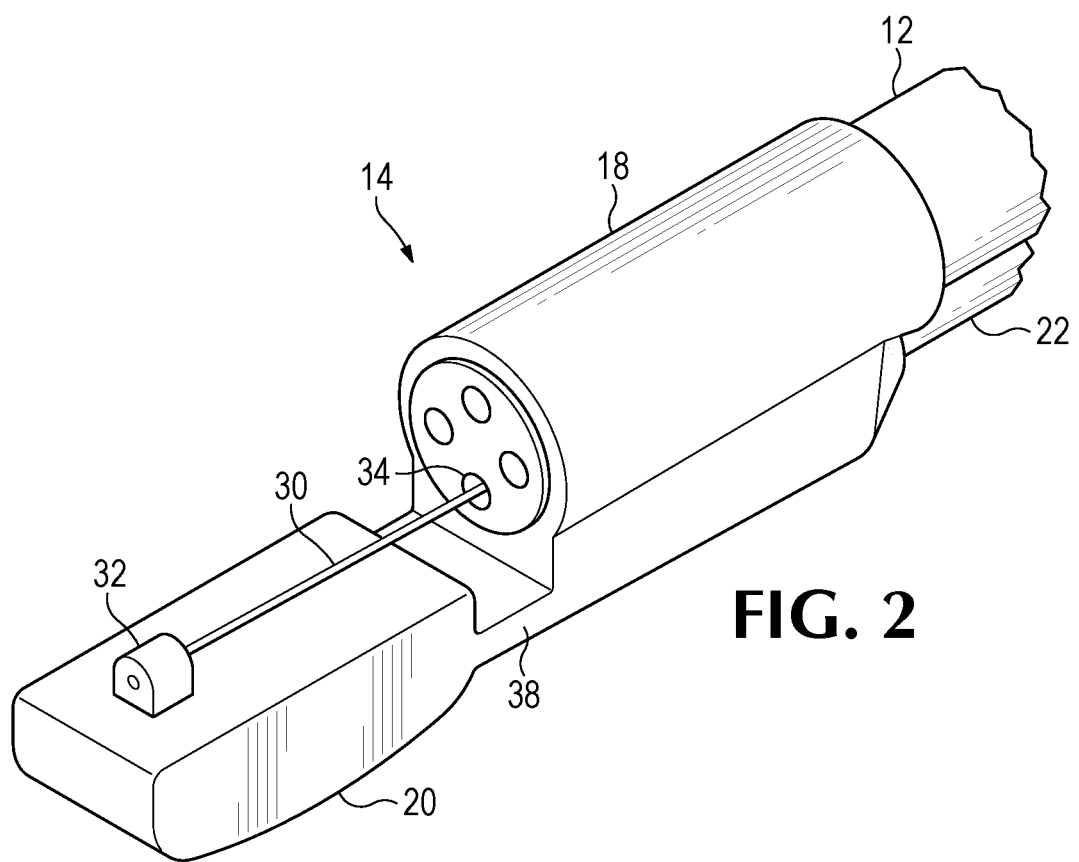

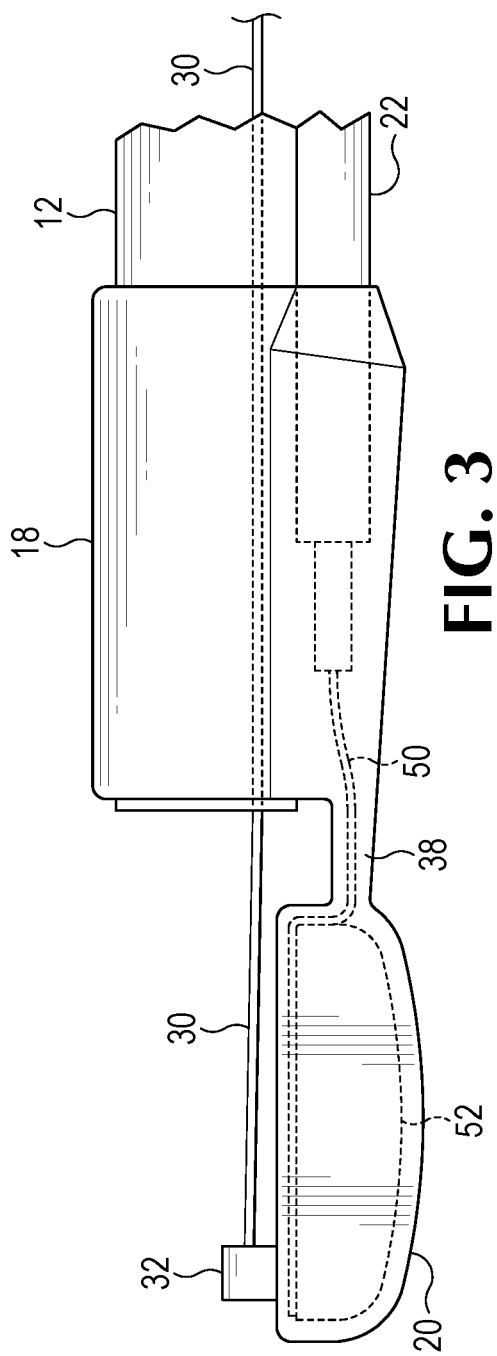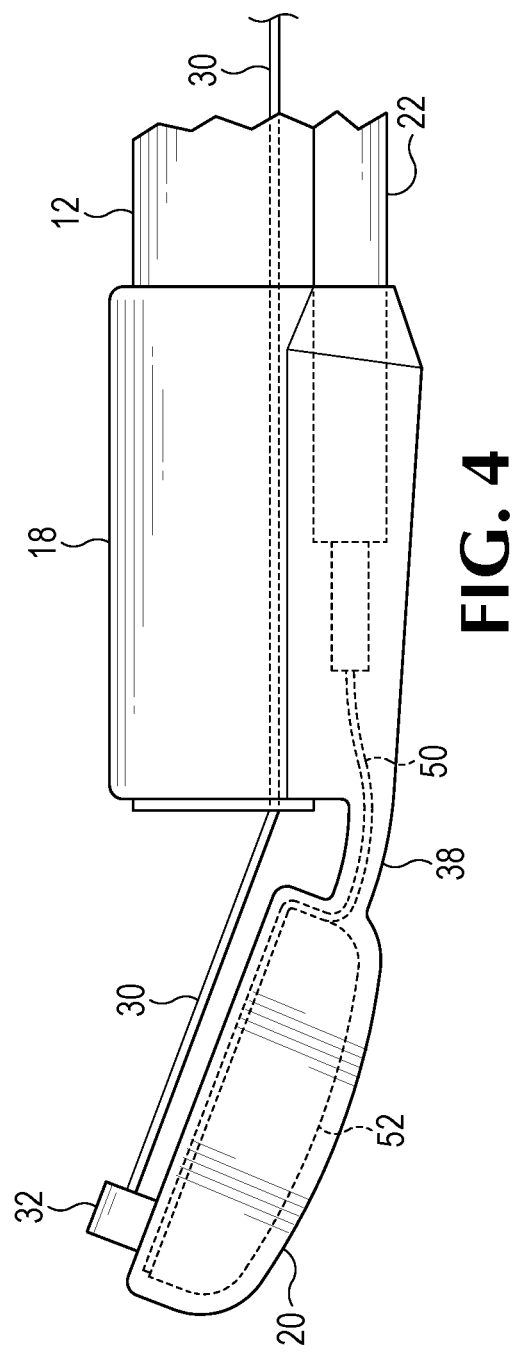

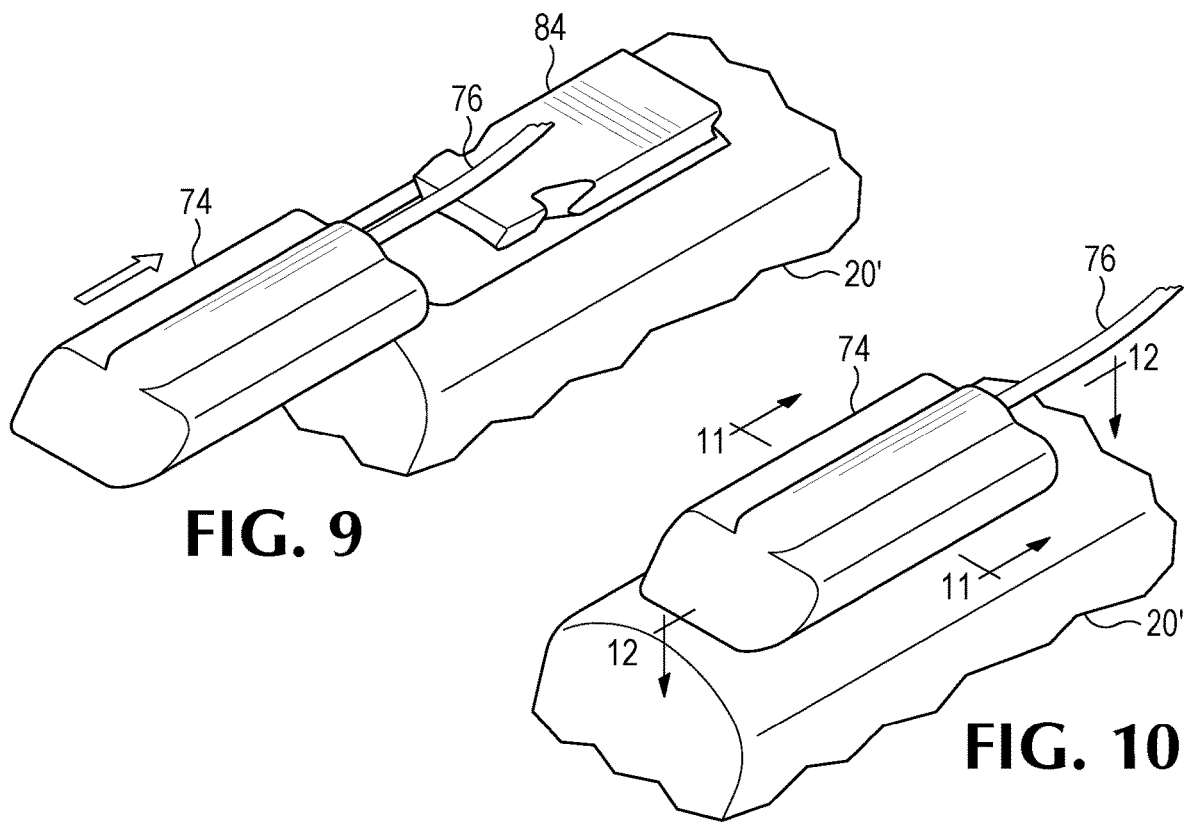
FIG. 9
FIG. 10
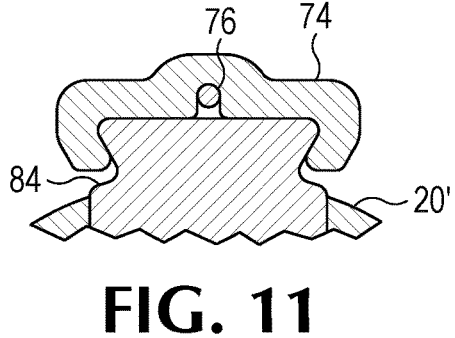
FIG. 11
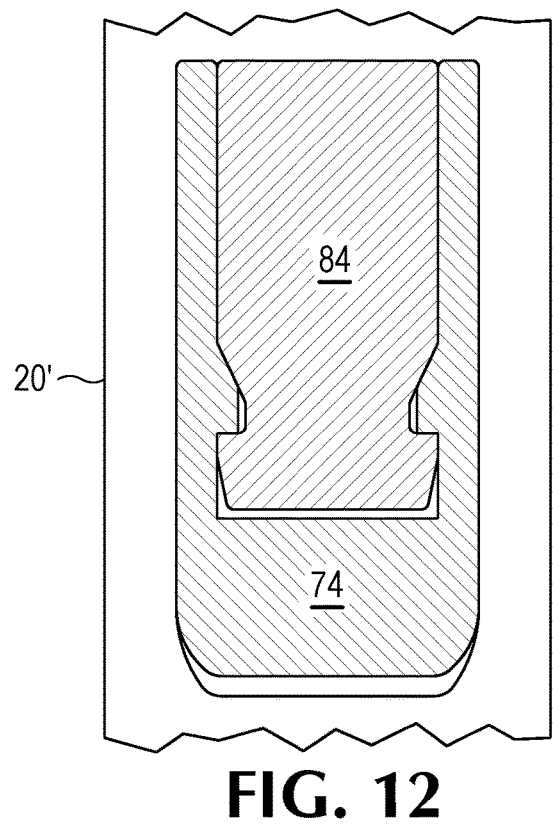
FIG. 12

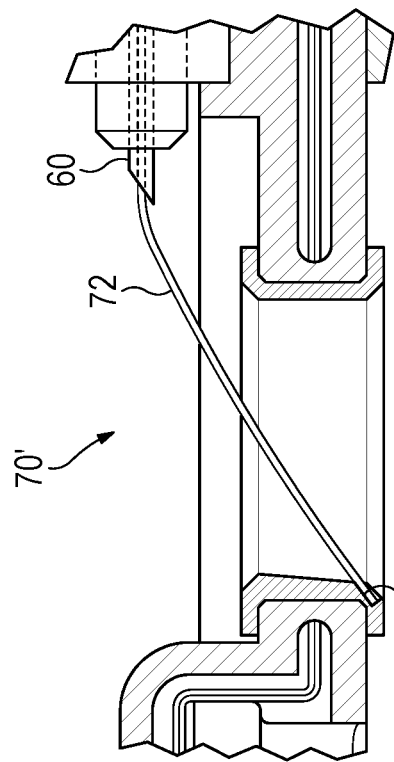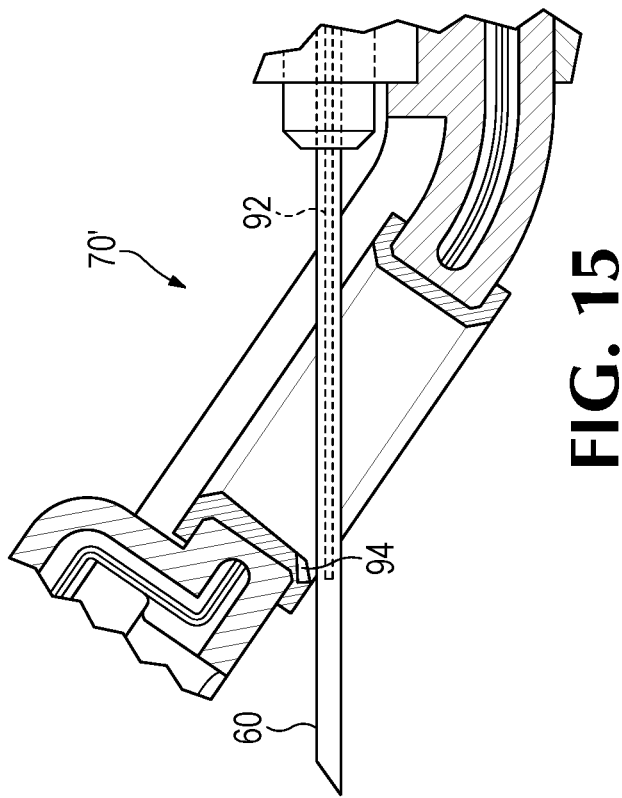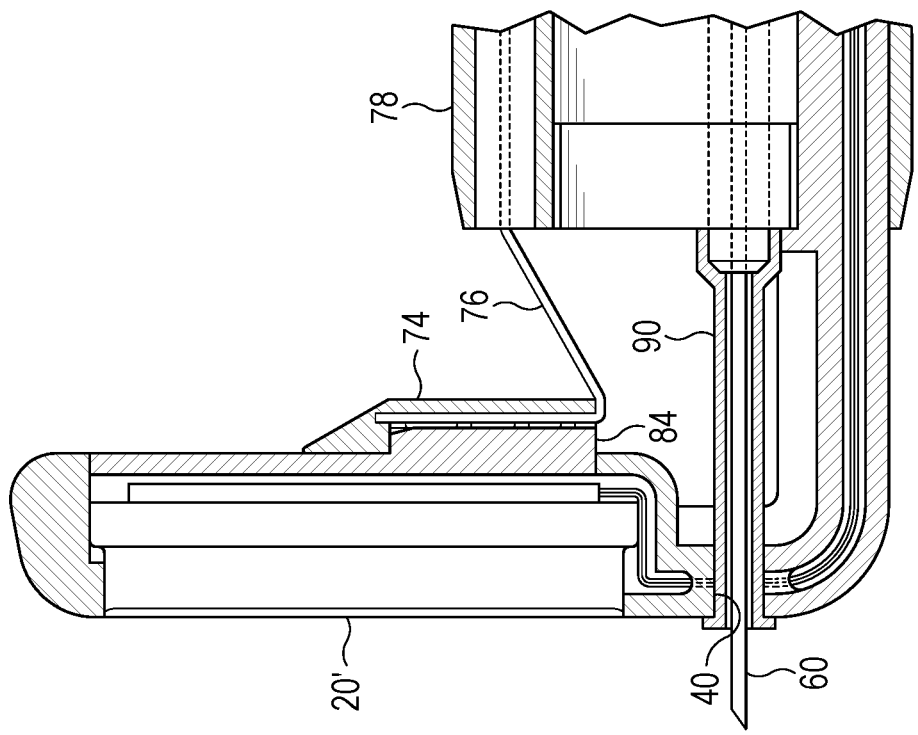

STEERABLE ULTRASOUND ATTACHMENT FOR ENDOSCOPE

RELATED APPLICATIONS

This application is a continuation of application U.S. Ser. No. 16/523,971, filed Jul. 26, 2019, which itself is a continuation-in-part of PCT international application PCT/US19/27331, filed Apr. 12, 2019, which itself is a continuation of application U.S. Ser. No. 15/951,347 filed Apr. 12, 2018, now U.S. Pat. No. 10,363,014, issued Jul. 30, 2019, all of which are incorporated by reference as if fully set forth herein.

BACKGROUND

1. Field of the Invention

The Invention is in the field of ultrasound imaging add-on equipment for endoscopes.

2. Background Art

Endoscopic ultrasound has undergone a rapid pace of development, now being used for the diagnosis and treatment of a wide variety of medical problems. As an endoscope can reach a location in the intestinal tract, closer than any skin surface, there is an opportunity to image from a closer location, and to obtain a tissue sample, using a biopsy needle and implement a variety of treatments. But due to an expense of greater than $300,000 for a complete system, endoscopic ultrasound systems are generally restricted to major hospitals. Endoscopes, however, are used in physicians' offices, most outpatient surgery centers and virtually all hospitals.

One type of endoscope is an upper endoscope, used to image and take tissue specimens from the upper GI tract. In this type of endoscope, if a needle is used to collect a specimen, it is typically advanced straight out of an endoscope lumen in a distal direction. Other types of endoscopes are bronchoscopes for viewing air passageways in the lungs and colonoscopes for viewing the colon.

Yet another type of endoscope is a duodenoscope, designed to be introduced into the duodenum (the upper part of the small intestines), and typically used to perform endoscope retrograde cholangiopancreatography (ERCP), in which the ducts of the pancreas and liver are imaged. Duodenoscopes are also used to gather tissue biopsies from sites in the duodenum, including the bile ducts. Duodenoscopes typically have a tip that houses a light, a video camera, and an instrument guide that can be tilted by an operator to control the angle at which the instrument (needle or other type of instrument) advances. Although the video camera and light can produce imagery that may help the endoscopist visualize potential targets directly, ultrasound imagery, when available, provides a different, dramatically expanded view of the regional anatomy. An ultrasound add-on for endoscopes has been described, but its capabilities are limited in that the viewing angle of the imaging head cannot be adjusted, and it does not provide for tissue sampling.

A problem faced by practitioners in the field of endoscopy is the thorough disinfection of the endoscope, between uses. As many endoscopes, in particular duodenoscopes, have some mechanical complexity, introducing a sterilizing material into the small spaces defined by these mechanisms, creates a huge challenge. Recently, an endoscope mechanism, having an instrument angle adjustment mechanism that is removable and disposable has been introduced, addressing many of these issues.

SUMMARY

In a first separate aspect, the present invention may take the form of an ultrasonic endoscope assembly, having an endoscope defining one or more lumens, and a needle that can be pushed forward out of a lumen, to collect a biopsy specimen. An ultrasound sub-assembly is attached to the endoscope and includes a communications cable, including a set of signal pathways, and having a distal end and an ultrasound imaging head connected to the distal end of the cable. Also, included is an imaging head movement sub-assembly, including a conduit that is releasably connected to the endoscope. The conduit contains a tension member that is releasably connected to the imaging head. Accordingly, the imaging head movement sub-assembly can be released from the endoscope and the imaging head, to be processed separately, after use.

In a second separate aspect, the present invention may take the form of an endoscope add-on assembly adapted to be attached to a target endoscope. The assembly includes an ultrasound imaging sub-assembly, including a communications cable connected to an ultrasound imaging head and an imaging head movement sub-assembly, including a conduit, holding a tension member that is attached to the ultrasound imaging head. Further included are connective elements, adapted to permit the endoscope add-on assembly to be attached to the target endoscope. Finally, the imaging head movement sub-assembly is detachable from the ultrasound imaging sub-assembly, thereby permitting the imaging head movement subassembly to be processed separately from the ultrasound imaging sub-assembly, after use.

BRIEF DESCRIPTION OF THE DRAWINGS

Exemplary embodiments are illustrated in referenced drawings. It is intended that the embodiments and figures disclosed herein are to be considered illustrative rather than restrictive.

FIG. 2 is an isometric view of the distal end of the assembly of FIG. 1.

FIG. 3 is a side view of the distal end of the assembly of FIG. 1, in a first position.

FIG. 4 is a side view of the distal end of the assembly of FIG. 1, in a second position.

FIG. 9 is a detail view of a portion of the assembly of FIG. 7, showing two of the parts disassembled from each other.

FIG. 10 is the detail view of FIG. 9 but showing the two parts joined.

FIG. 11 is a sectional view taken along line 11-11, of FIG. 10.

FIG. 12 is a sectional view taken along line 12-12 of FIG. 10.

FIG. 13 is a sectional view of the tip of the assembly of FIG. 7, showing the needle guide used to guide a needle.

FIG. 14 is a sectional partial view of the assembly of FIG. 7 having a different style of needle guide.

FIG. 15 is a view of the assembly of FIG. 14, showing the needle guide in use.

DETAILED DESCRIPTION OF THE PREFERRED EMBODIMENTS

Definition

As used in this application, the term "endoscope" refers to an illuminated optical, typically a slender and tubular instrument used to look deep into the body and used in procedures referred to as "endoscopy". This term encompasses, but is not limited to upper endoscopes, duodenoscopes, colonoscopes and bronchoscopes, as well as devices referenced simply as "endoscopes".

DETAILED DESCRIPTION OF THE PREFERRED EMBODIMENT

Figure 1:
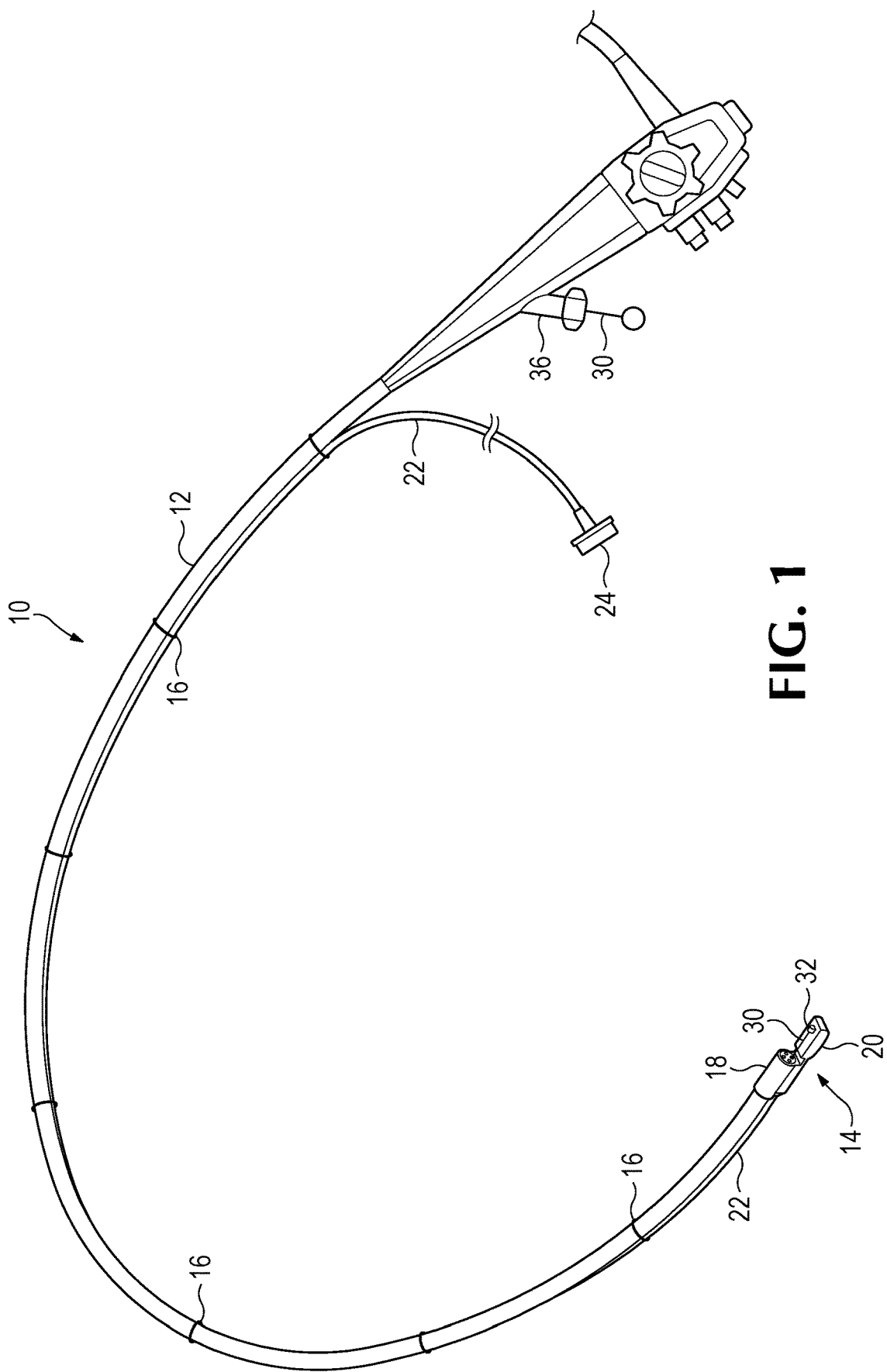
FIG. 1 is an isometric view of an imaging assembly having an endoscope and an ultrasound imaging assembly added on, according to a preferred embodiment of the present invention.

In a first preferred embodiment, an imaging assembly 10 includes an upper endoscope 12 and an ultrasound assembly 14 that has been attached to endoscope 12 by means of retaining element 18, integral to ultrasound assembly 14. In an alternative preferred embodiment, a retaining element is provided that is separate from ultrasound assembly 14 but works cooperatively to retain assembly 14 on endoscope 12. Assembly 14 also includes an ultrasound imaging (also referred to as "transducer") head 20 that is electrically connected to a multiple signal pathway cable 22 by way of a flex circuit 50 (which is also a form of a signal pathway cable), that includes a set of parallel electrical leads, which may be traces. Cable 22, which has a multiplicity of signal pathways extending therethrough terminates in a connector 24, adapted to connect to an imaging station. Elements 16, which may be rubber bands, or some other form of elastic bands or clips, help to retain cable 22, to the side of endoscope 12. A tension member 30, such as a wire (which may also have some compressive strength) is attached to a fixation point 32 on ultrasound imaging head 20 and extends through a lumen 34 (FIG. 2) to emerge outside of a port 36 on the proximal end of endoscope 12, to be manipulated. In embodiments, tension member 30, does not extend through lumen 34, but extends along the side of endoscope 12, and in some embodiments is retained by elements 16, which are modified from the simple shapes shown in FIG. 1, to include eyelets, to create a guide path for tension member 30. In one embodiment, tension member 30 is connected to controls on the proximal end of endoscope 12, to facilitate manipulation. In embodiments, these controls may take the form of a spool, that can be easily let out, or drawn in. Endoscope 12 also is equipped with intrinsic controls for deflecting the tip of the insertion tube, to facilitate introduction to a site of interest.

In an alternative embodiment, tension member 30 is replaced by a tension member extending along the exterior of the endoscope, to a fixation point on the end of the endoscope. A physician may exert traction or pulsion on tension member 30 in any one of a variety of ways, to cause ultrasound imaging head 20 to bend forward or back toward retaining element 18, as permitted by a resiliently flexible neck 38 (FIG. 2). In one method a rotatable element is used to draw in tension member 30 or push it out.

In preferred embodiment endoscope 12 includes an element at its distal end to guide the alignment of the retaining element 18. For example, endoscope 12 many include a groove at its distal end, into which a key element on retaining element 18 engages. In another embodiment, an orientation guide includes a peg that fits into the lumen 34 and is used to guide the correct orientation of retaining element 18. In one embodiment, assembly 14 is made for intended disposal, after a single use, and is used in this manner. In another embodiment, assembly 14 is constructed so as to be prepared and/or cleaned appropriately for reuse, after use, and then reused. Although until recently generally disinfection procedures were deemed adequate, the detection of instances of the spread of infection through endoscope has given rise to the use of high-end disinfection techniques for endoscopes. These disinfection techniques make use of chemicals to kill any pathogens left on the scope after use. Other disinfection or sterilization techniques may be used, including processing using of UV light and/or a gas, such as ozone. In the context of this application, the term "cleaning" encompasses all disinfection and sterilization techniques. Generally, the materials used in endoscopes are such that autoclaving an endoscope, or an attachment thereto is not feasible.

Figure 5:
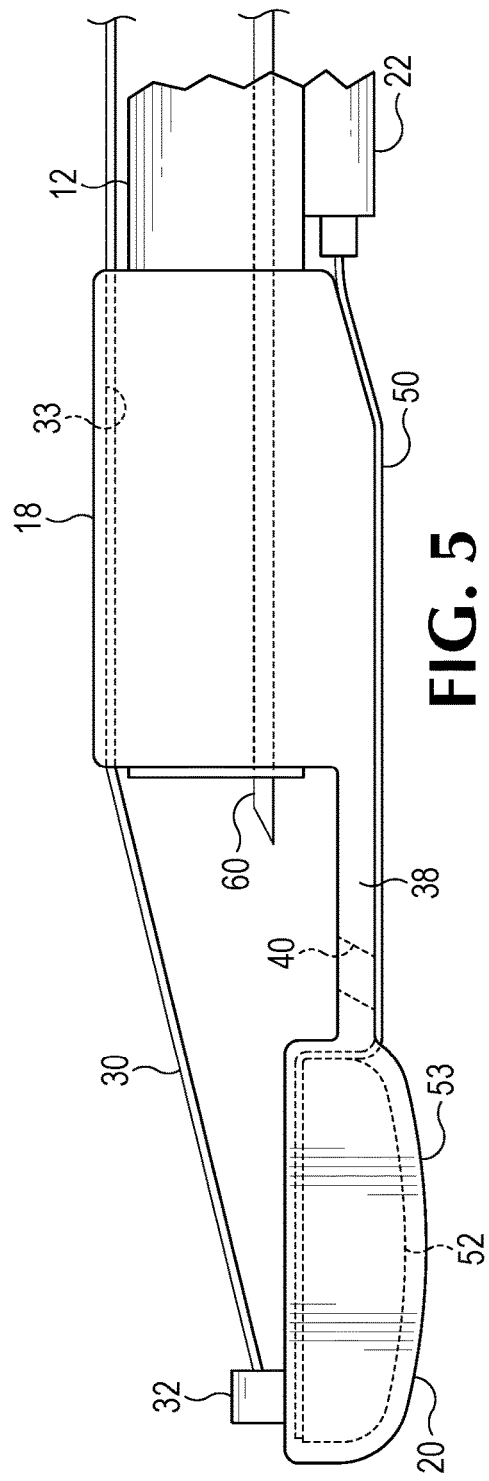
FIG. 5 is a side view of the distal end of an alternative embodiment of an imaging assembly.
Figure 6:
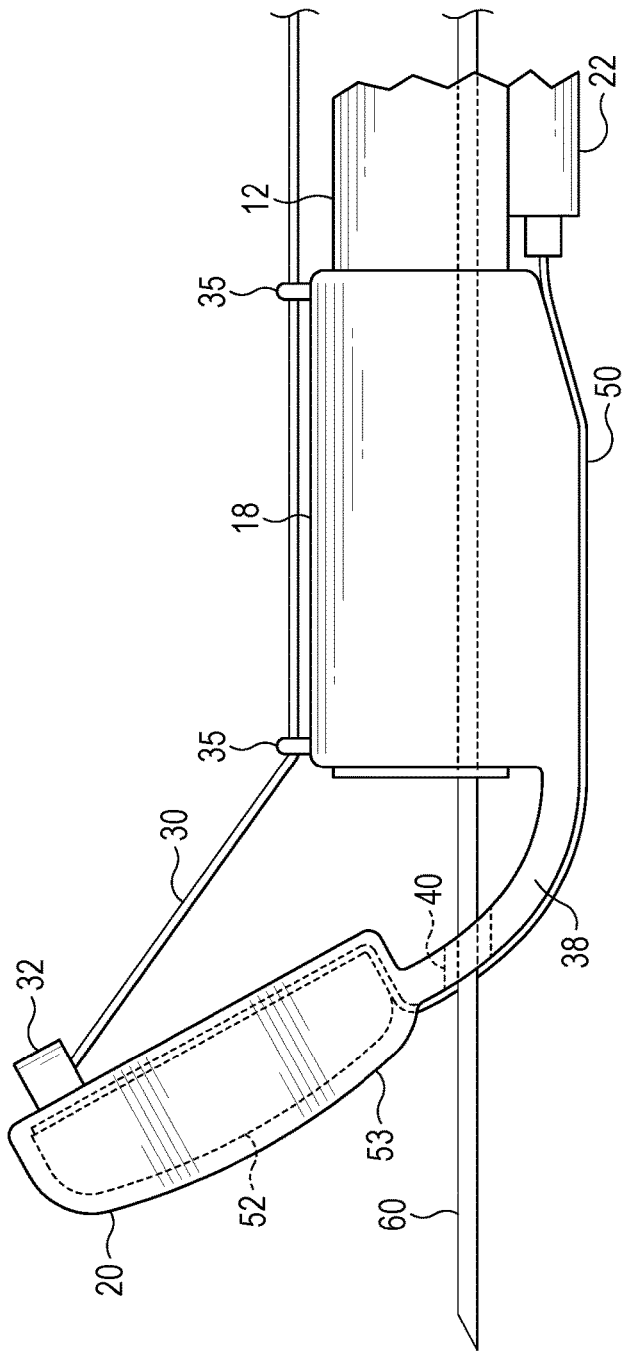
FIG. 6 is a side view of another alternative embodiment of an imaging assembly.

Referring to FIGS. 3 and 4, a flex circuit 50, which passes through the flexible neck 38, electrically connects imaging head 20 to cable 22. Flex circuit 50 has an electrical lead for each transducer element in an ultrasound element array 52, resident in the ultrasound imaging head 20, to drive ultrasound element array 52 and relay signals from it. Array 52 is covered with a protective coating 53 (FIGS. 5 and 6). In an alternative preferred embodiment, flex circuit 50 extends from imaging head 20 to (or through) connector 24, may define a plurality of coax cables and may directly contact the elements of the ultrasound array 52. In another alternative embodiment, cable 22 comprises a set of coax cable bound together with an adherent and protective substance, such as a polymer, and extends from connector 24 to imaging head 20. In yet another embodiment, a fiber optic cable is used in place of cable 22, with light to electric convertors at its distal end. In any one of these arrangements elements 22 and 50 could be termed separately or in combination as a multiple signal pathway cable.

In a preferred embodiment, a biopsy needle 60 (FIGS. 5 and 6), which forms the sharpened, distal portion of a long, flexible, hollow-core wire, is provided. This wire is sheathed in a flexible conduit (not shown), thin enough to extend through the lumen 34 and protecting endoscope 12 from being damaged by needle 60. Once the conduit reaches the distal end of endoscope 12, it may be pushed out to extend from lumen 34, and provide further guidance for needle 60, which is pushed out of the conduit at a point distal to the end of endoscope 12. Alternatively, the conduit may be pushed roughly to the end of lumen 34, with the needle 60 pushed out of the conduit at that point.

Referring to FIG. 5, in an alternative preferred embodiment tension member 30 extends through a channel 33 in retaining element 18 to reach fixation point 32. This figure also shows a needle 60 that has been pushed through a lumen of the endoscope 12 and is emerging from the distal end of the lumen. An aperture 40 is defined in neck 38, corresponding to an aperture in flex circuit 50, aligned with aperture 40. FIG. 6 shows an embodiment that is similar to that of FIG. 5, but instead with tension member 30 extending through a pair of eyelets 35, supported on the retaining element 18. As well as showing a slightly different embodiment, FIG. 6 also shows imaging head 20 retracted and needle 60 extending through aperture 40, as it would be in order to take a biopsy. Notably, in this position the needle would be within the field of view of ultrasound array 52. In embodiments, tension member 30 can pull head 20 into an obtuse angle, relative to the distal end of the endoscope 12. Generally, aperture 40 is in the shape of a long oval, so that the needle 60 can pass through it over a long range of degree of bending of neck 38. In another preferred embodiment, the flexible conduit is extended distally from lumen 34 into a v-shaped indentation (not shown) on surface of flexible neck 38, aligning the conduit so that the needle 60 is aligned to pass through aperture 40.

To use imaging assembly 10, ultrasound assembly 14 is attached to endoscope 12 by means of retaining element 18. In an alternative embodiment, rubber bands or clips 16 (FIG. 1) retain cable 22 to the side of endoscope 12. Imaging head 20 is then delivered to an area of interest, by means of standard endoscope introduction techniques. Imaging head 20 may then be moved to gain imagery of the area of interest by dedicated controls which control the ultrasound imaging head 20 deflection. If there appears to be a finding to be sampled, needle 60 may be introduced through an endoscope lumen and through aperture 40 and used to take a biopsy, inject a drug, or otherwise effect a medical procedure. Finally, needle 60 is retracted through the lumen of endoscope 12 and the endoscope is retrieved from the patient's body. In other embodiments, needle 60 is not included and an assembly that is similar to imaging assembly 10 but without needle 60 and related elements, is used for imaging alone, or for introduction of some other device.

FIGS. 7-13 show an alternative embodiment 70 of the assembly 10, with the further innovation of a disposable head-movement sub-assembly 72, which includes a head clip 74, a movement cable 76, a cable clip 78 and a conduit 80, holding the major portion of movement cable 76. A clip-hold 84 is defined on the back of imaging head 20'. Further, the cable clip 78 holds imaging head and other portions of the ultrasound assembly 14', including communicative cable 22', to the endoscope 12. FIGS. 9-12 show engagement of head clip 74 to clip-hold 84. FIG. 9 shows head clip 74 distal to and being pulled back onto clip-hold 84, with FIG. 10 showing head clip 74 engaged to clip-hold 84 and FIGS. 11 and 12 showing different sectional views of head clip 74 and clip-hold 84 engaged together.

Figure 7:
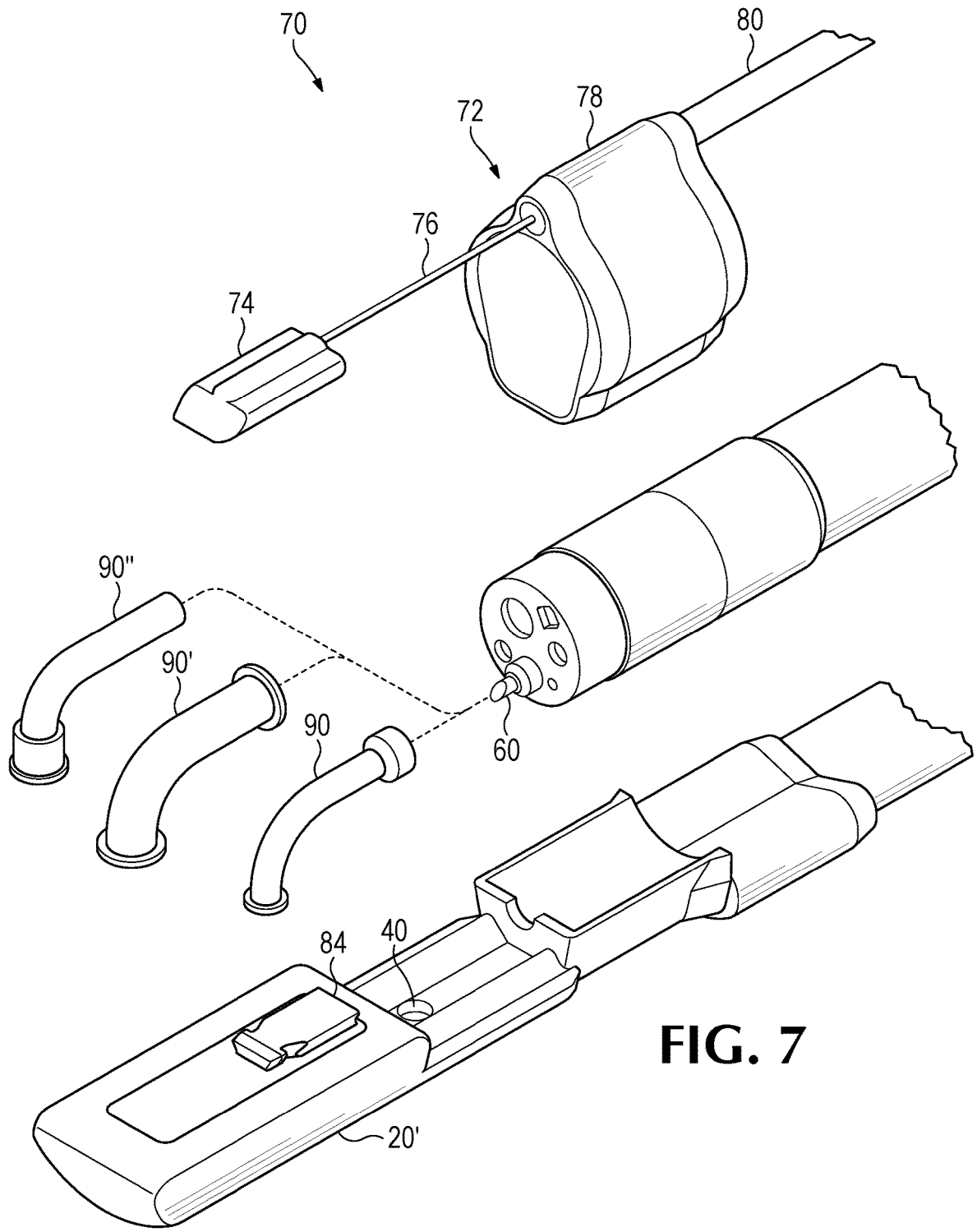
FIG. 7 is an alternative embodiment of an imaging assembly, having an ultrasound imaging sub-assembly that includes an ultrasound head movement assembly that is detachable, and showing three alternative needle guides.
Figure 8:
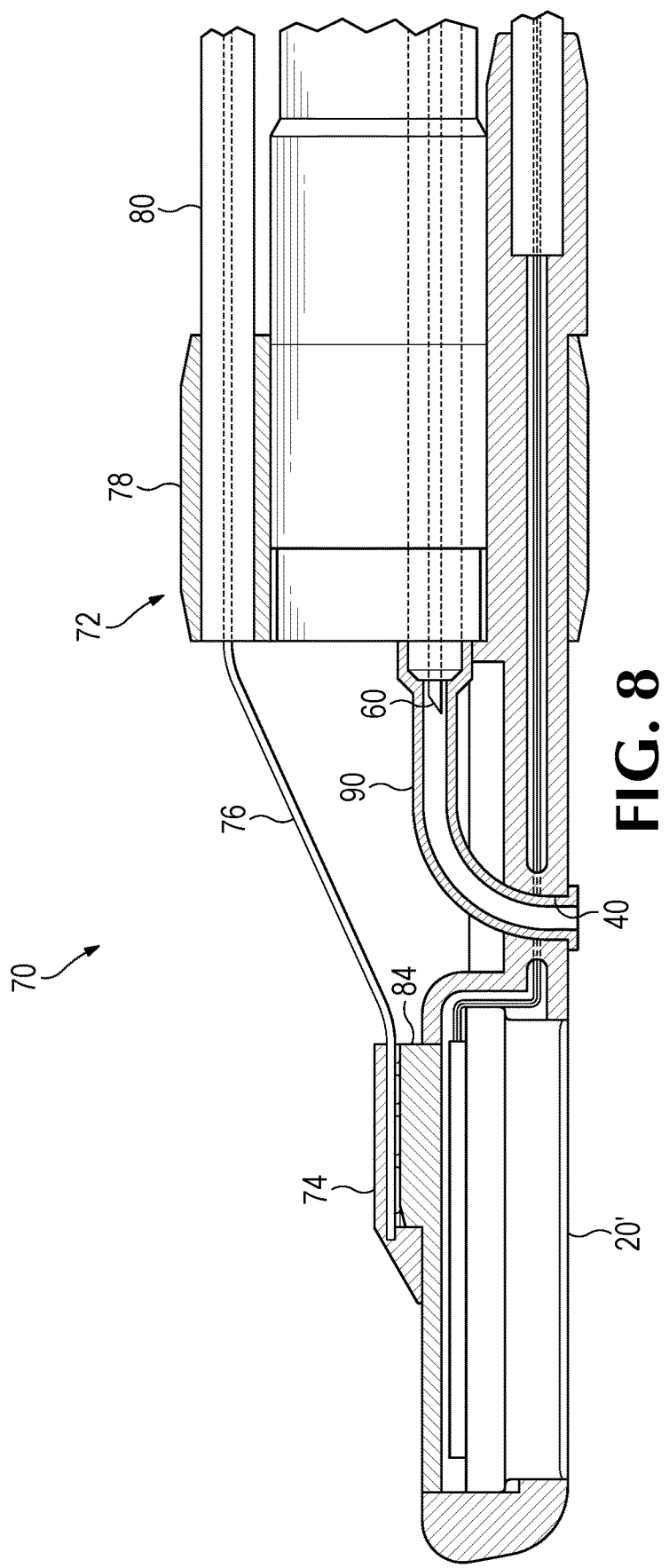
FIG. 8 is a sectional view of a of the assembly of FIG. 7, showing a needle guide in a deployed state.

Another difference between assembly 70 and assembly 10 is the optional presence of a needle guide 90. FIG. 7 shows two additional variant needle guides 90' and 90". In assembly 10 it is possible that a needle 60 pushed out of a lumen of endoscope 12 could miss the aperture 40 in neck 38 and be blocked by neck 38 from further advancement. This might happen if a user attempted to push needle 60 into use when the neck 38 was not sufficiently pulled back, to bring aperture 40 into the correct position to let needle 60 pass through. The result could be damage caused to imaging head 20', cause by needle 60. A needle guide 90 engages with aperture 40, so that needle 60 will be guided to aperture 40 with certainty, or will be blocked by guide 90, when head 20' is not positioned correctly to align aperture 40 with the path of needle 60. FIG. 13 shows a needle guide 90 in use as head 20' is pulled fully back, to a forward-looking position as needle 60 is advanced through aperture 40, with the assistance of guide 90. It is a further advantage of assembly 70 (and assembly 10) that the head 20' can be moved to a forward-looking position as shown in FIG. 13, which is helpful to surgeons for some types of procedures. Referring to FIGS. 14 and 15, in a variant 70' to assembly 70, a needle guide 92 is provided in the form of a wire that needle 60 advances over. When not in use, needle guide 92 is retained in a needle-guide notch 94 (FIG. 15).

Figure 16:
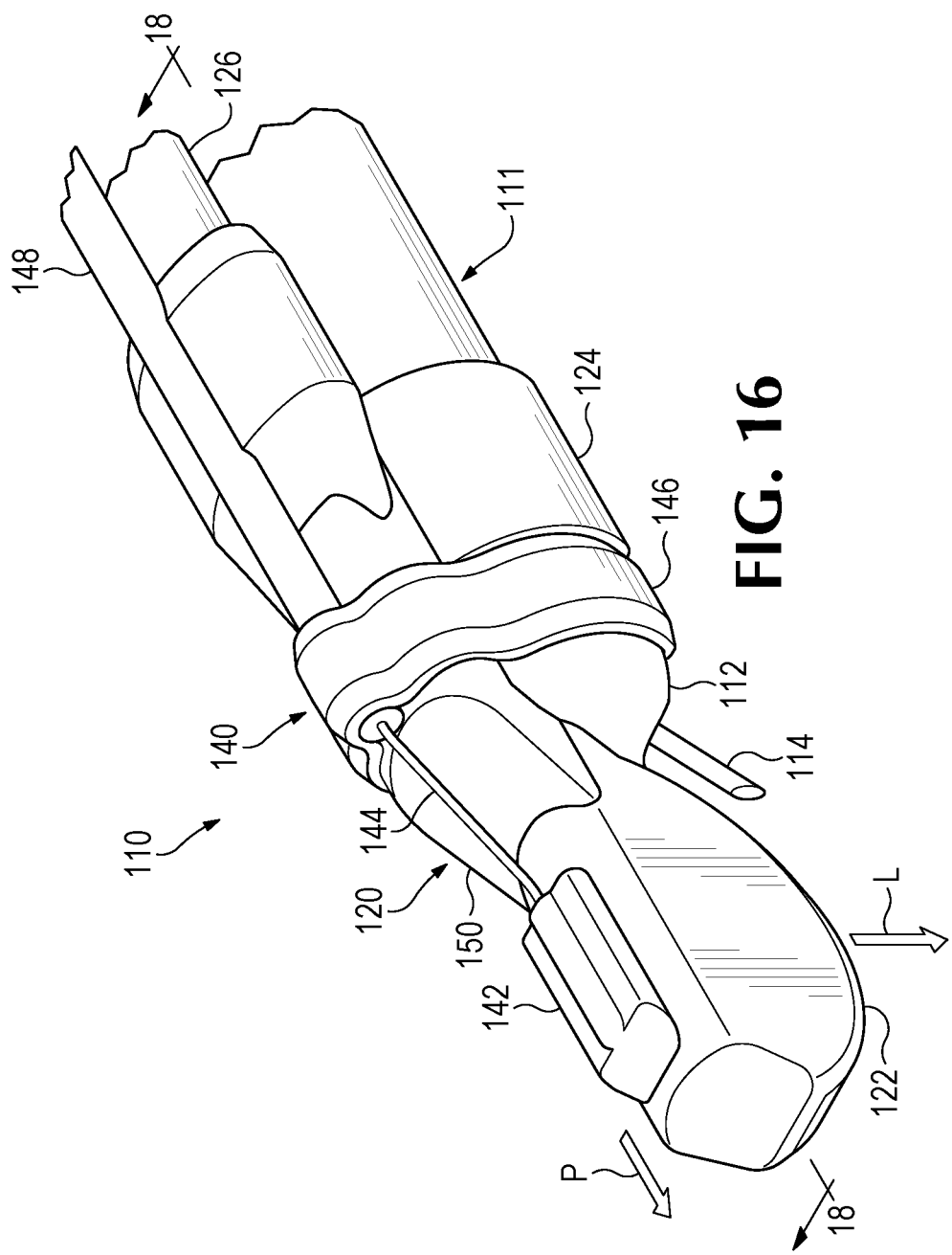
FIG. 16 is an isometric view of a duodenoscope assembly, having an ultrasound imaging sub-assembly.
Figure 17:
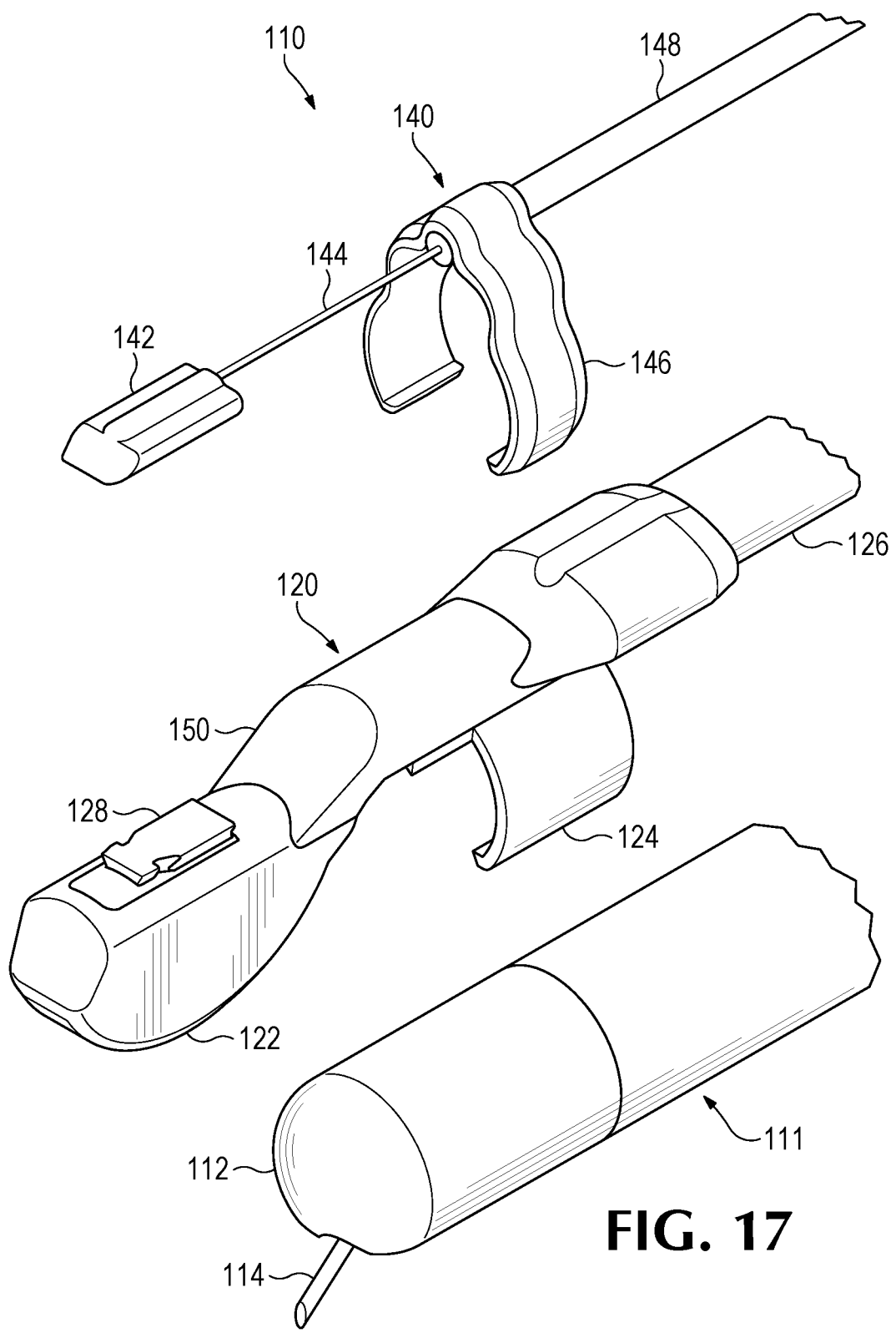
FIG. 17 is an isometric view of the assembly of FIG. 16, in a disassembled state.
Figure 18:
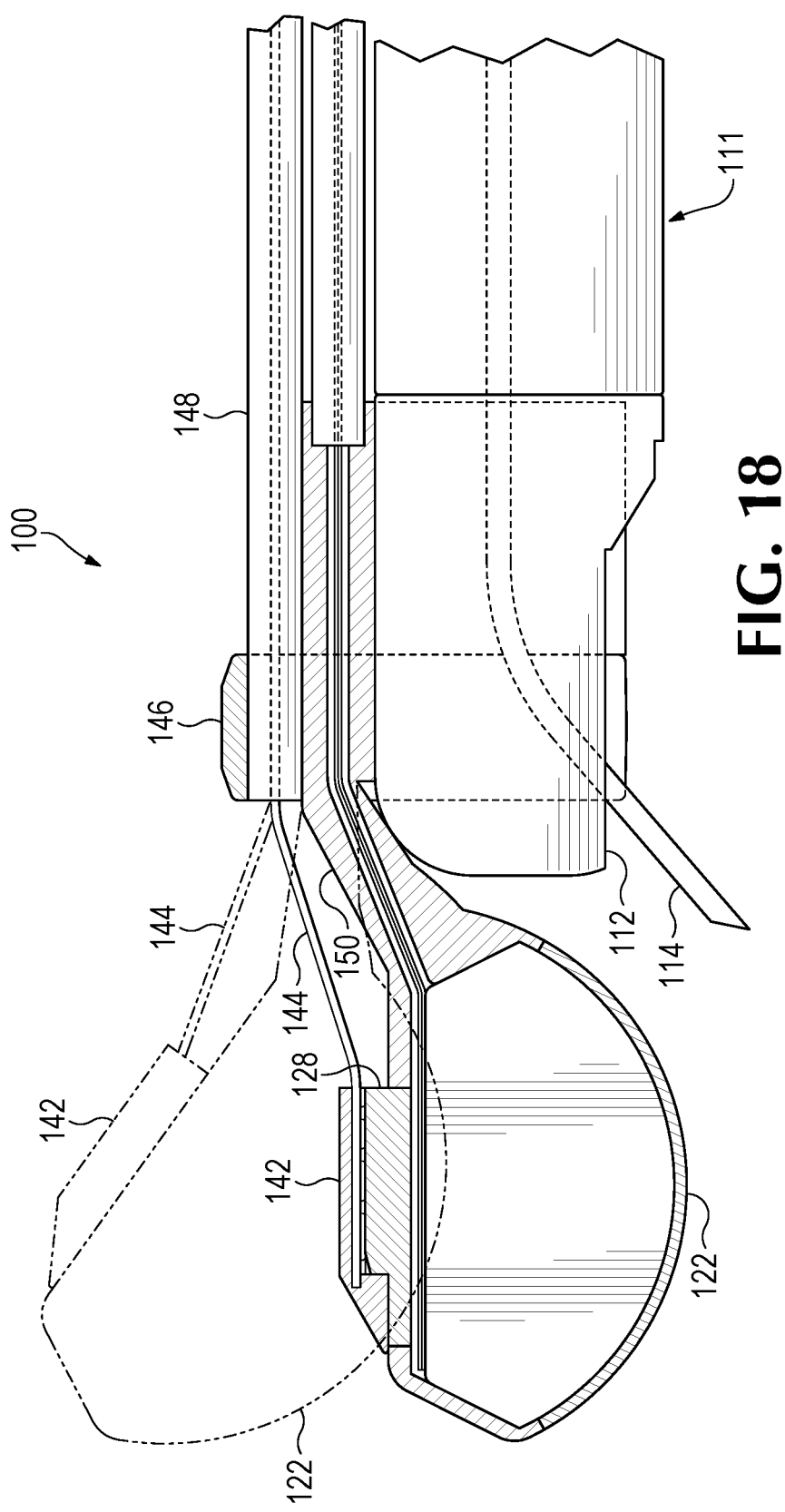
FIG. 18 is a sectional view of the assembly of FIG. 16, showing a different position for a portion of the assembly, in dashed line.

Referring now to FIGS. 16-18, a duodenoscope assembly 110 includes a duodenoscope 111 having a single-use instrument guidance head 112 (shown most clearly in FIG. 18), having an instrument guide 114 extending outwardly at an angle between a first lateral direction L and the distal direction P. Guidance head 112 can change the direction of guide 114, in response to varying user input via a tension member and an instrument variable guide member (not shown). Referring to FIG. 16, a cable/head sub-assembly 120 includes an ultrasound imaging head 122, a scope clip 124, a multiple signal pathway cable 126, delivering signals to imaging head 122 and relaying signals from imaging head 122. The signal pathways of cable 126 may be electrical conductors, and more specifically may each be a coax cable or a trace on a flex circuit. Other forms of signal pathways are possible. Imaging head 122 is shown having a signal emission surface facing the first lateral direction L, and a clip-hold 128 (FIG. 17) is present on head 122 on a side displaced from said signal emission surface in a second lateral direction, opposed to said first lateral direction L. An imaging head movement sub-assembly 140 includes a head clip 142, shaped to engage to clip-hold 128, a movement cable 144 a cable clip 146 and a conduit 148, holding the major portion of movement cable 144. Referring to FIG. 18 when cable 144 is pulled it pulls back imaging head 122 as indicated by the dotted line. In some embodiments sub-assembly 140 further includes an actuator (not shown) at the proximal end, to permit an operator to draw in cable 144, thereby pulling on imaging head 122 or let out cable 144, either pushing on imaging head 122 or permitting the resiliency of the material of cable 126 to place head 122 into a position more aligned with the longitudinal dimension of the duodenoscope 111, at its distal end. The actuator of cable 144 may take the form of a wheel, a lever or any other arrangement convenient to the user.

Because disinfection techniques typically require the application of chemicals in liquid form, thin crevices, into which liquid might not easily flow are generally undesirable. Accordingly, clip-hold 128 is designed so as not to define thin crevices with the imaging head 122. In alternative preferred embodiments, clip-hold 128 may have a shape that is similar to a knob, to further avoid defining any narrow crevices.

As noted in the background, the disinfection of devices such as assembly 110 is a matter of great concern, as there have been cases of the spread of strains of bacteria that are resistant to multiple antibiotics, by way of duodenoscope reuse. One area which may prove particularly difficult to sterilize is conduit 148, as movement cable 144 will tend to introduce body fluids into conduit 148 as cable 144 is pulled back into conduit 148, as imaging head 122 is moved back. To address this issue head movement sub-assembly is releasable and removable from the remainder of assembly 110 and is made to be inexpensive enough to use a single time and then be disposed. This eliminates the possibility of infection being spread from patient to patient by way of sub-assembly 140. Cable/head sub-assembly 120 does not have a similar structure that would provide a hard-to-reach place that would make disinfection difficult and will tend to be more expensive as it must contain a multiplicity of fine wires or other forms of signal pathways. Accordingly, cable/head sub-assembly 120 is designed to be cleaned and reused.

Before performing an endoscopic (duodenoscopic) procedure the endoscopist would obtain an unused head movement sub-assembly 140 and attach it to the remainder of assembly 110. After use, the user detaches and disposes sub-assembly 140.

Referring to FIG. 16, movement cable 144 may be pulled back to cause head 122 to face in a more distal facing direction. Pushing cable 144 forward causes head 122 to adopt a lateral viewing angle as shown, in one embodiment due to resilience of neck 150, but in another due to stiffness and compressive strength in cable 144.

Figure 19:
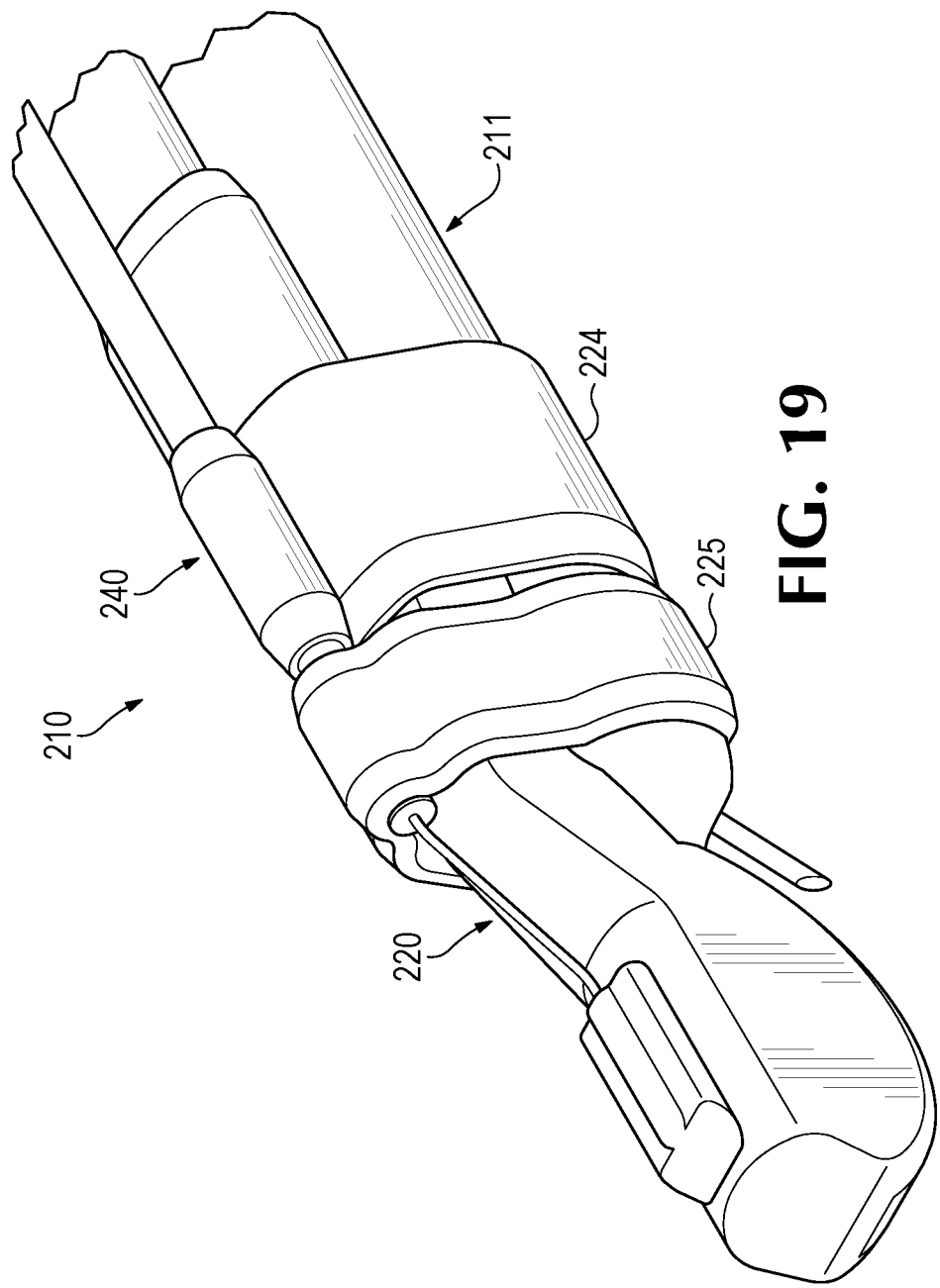
FIG. 19 is an isometric view of an alternative embodiment of a duodenoscope assembly.
Figure 20:
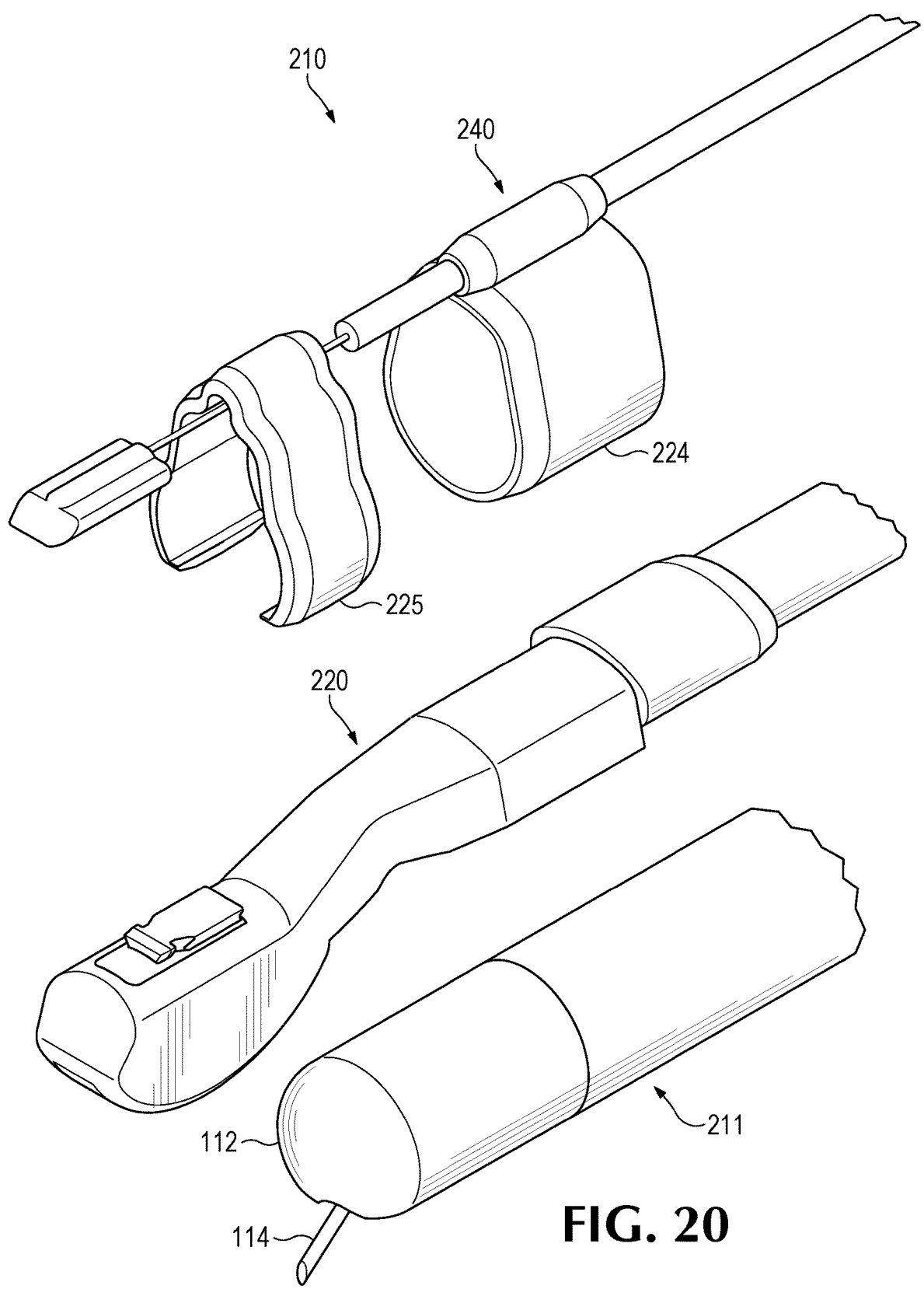
FIG. 20 is an isometric of the assembly of FIG. 19, in a disassembled state.

Referring to FIGS. 19 and 20, in an alternative preferred embodiment of a duodenoscope assembly 210, a holder 224 encompasses together both the duodenoscope 211, the cable/head sub-assembly 220 and the imaging head movement sub-assembly 240. A clip 225 also helps to hold the elements together.

In an additional set of embodiments and methods of use, any one of assembly 14 (combined with tension member 30), and assembly 70 and the combination of assemblies 120 and 140, can be made so that the resultant assembly 14/30, 70 or 120/140 (henceforth collective designated as assembly 14') is produced and sold with a recommended method of use to dispose the entire assembly after a single use. This may greatly simplify health facility operations. In a preferred embodiment, the ultrasound array 52 (or the array in imaging head 20' or 122) is a capacitive micromachined ultrasonic transducer (CMUT), which is generally less expensive than a piezoelectric transducer. Because cleansing an ultrasound assembly 14' can be so cumbersome and expensive, and because of the great value of the surgeries being performed, even an assembly 14' selling for upwards of $2,000 in 2019, could be more economical to dispose of, than to be cleansed and reused. In one embodiment of an assembly 14', the number of array elements is reduced, from for example 256, to for example 128, or even to 64, to reduce the cost of the array, and the signal pathways leading to and from the array.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An ultrasonic endoscope assembly, comprising:
   a) an endoscope defining one or more lumens, and a needle that can be pushed forward out of a said lumen, to collect a biopsy specimen;
   b) an ultrasound sub-assembly, attached to said endoscope and including:
      i) a communications cable including a set of conductors, having a distal end;
      ii) an ultrasound imaging head connected to said distal end of said cable, wherein said ultrasound imaging head comprises a clip-hold;
   c) an imaging head movement sub-assembly, including a conduit that is releasably connected to said endoscope via a cable clip, said conduit containing a wire terminating in a head clip configured to engage said clip-hold, wherein said wire is releasably connected to said ultrasound imaging head by selective engagement and disengagement of said head clip from said clip-hold; and
   d) whereby said imaging head movement sub-assembly can be released from said endoscope by detaching said cable clip from said endoscope, and whereby the selective disengagement of said head clip from said clip-hold and the detachment of the cable clip from said endoscope enables the processing of said endoscope, said imaging head movement sub-assembly, and ultrasound sub-assembly separately, between different uses.

2. The assembly of claim 1, wherein said endoscope is a duodenoscope, further including a needle guidance head that can be controllably used to adjust the angle at which a needle is advanced from said lumen to collect a specimen.

3. The assembly of claim 2, wherein said needle guidance head is removeable.

4. The assembly of claim 1, wherein said ultrasound sub-assembly is releasable from said endoscope.

5. The assembly of claim 1, wherein said distal end of said communications cable forms a neck that bends when said imaging head movement sub-assembly is used to pull said imaging head.

6. An ultrasonic endoscope assembly, comprising:
   a) an endoscope defining one or more lumens, and a needle that can be pushed forward out of a said lumen, to collect a biopsy specimen;
   b) an ultrasound sub-assembly, attached to said endoscope and including:
      i) a communications cable including a set of conductors, having a distal end;
      ii) an ultrasound imaging head connected to said distal end of said cable;
   c) an imaging head movement sub-assembly, including a conduit that is releasably connected to said endoscope, said conduit containing a wire that is releasably connected to said ultrasound imaging head; and
   d) whereby said imaging head movement sub-assembly can be released from said endoscope and said imaging head, enabling processing of said endoscope and ultrasound sub-assembly separately, between different uses, wherein said distal end of said communications cable forms a neck that bends when said imaging head movement sub-assembly is used to pull said imaging head and wherein said neck defines an aperture, to let said needle pass through said neck.

7. The assembly of claim 6, wherein said endoscope includes a needle guide that can be used to direct a needle out of said scope so as to pass through said aperture.

8. An endoscope add-on assembly adapted to be attached to a target endoscope, including:
   a) an ultrasound imaging sub-assembly, including a communications cable connected to an ultrasound imaging head comprising a clip-hold;
   b) an imaging head movement sub-assembly, including a conduit, holding a wire terminating in a head clip configured to engage said clip-hold;
   c) a clip, adapted to permit said endoscope add-on assembly to be attached to said target endoscope;
   d) wherein said imaging head movement sub-assembly is detachable from said ultrasound imaging sub-assembly by disengaging said clip-hold from said head clip, thereby permitting said ultrasound imaging sub-assembly to be processed separately from said imaging head movement subassembly, between uses.

9. The assembly of claim 8, wherein said target endoscope is an upper endoscope.

10. The assembly of claim 8, wherein said target endoscope is a duodenoscope.

11. The endoscope add-on assembly of claim 8, wherein a distal end of said communications cable forms a neck that bends when said imaging head movement sub-assembly is used to pull said imaging head.

12. The endoscope add-on assembly of claim 11, wherein said neck defines an aperture, to let said needle pass through said neck.

\* \* \* \* \*